(12) United States Patent
Sanchez

(10) Patent No.: US 10,709,845 B2
(45) Date of Patent: Jul. 14, 2020

(54) DRUG DELIVERY DEVICE WITH A ROTATABLE DRIVE MECHANISM

(71) Applicant: AMGEN INC., Thousand Oaks, CA (US)

(72) Inventor: Steve Sanchez, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 371 days.

(21) Appl. No.: 15/651,720

(22) Filed: Jul. 17, 2017

(65) Prior Publication Data

US 2018/0021521 A1    Jan. 25, 2018

Related U.S. Application Data

(60) Provisional application No. 62/365,185, filed on Jul. 21, 2016.

(51) Int. Cl.
*A61M 5/315* (2006.01)
*A61M 5/20* (2006.01)

(52) U.S. Cl.
CPC ...... *A61M 5/31586* (2013.01); *A61M 5/2033* (2013.01); *A61M 5/31501* (2013.01); *A61M 2005/31588* (2013.01); *A61M 2205/103* (2013.01); *A61M 2205/3365* (2013.01)

(58) Field of Classification Search
CPC ............ A61M 5/31586; A61M 5/2033; A61M 5/31501; A61M 2005/103; A61M 2205/3365; A61M 39/16; A61M 2039/0285; A61M 39/162; A61M 39/165
See application file for complete search history.

(56) References Cited

U.S. PATENT DOCUMENTS

| 3,631,847 A * | 1/1972 | Hobbs, II ........... A61B 5/02755 |
| | | 600/432 |
| 4,860,744 A | 8/1989 | Johnson et al. |
| 4,945,727 A | 8/1990 | Whitehead et al. |
| 5,037,396 A | 8/1991 | Streeter |
| 5,176,646 A | 1/1993 | Kuroda |
| 5,807,323 A | 9/1998 | Kriesel et al. |
| 6,447,482 B1 | 9/2002 | Rønborg et al. |
| 6,589,210 B1 | 7/2003 | Rolfe |
| 6,755,026 B2 | 6/2004 | Wallach |

(Continued)

*Primary Examiner* — Nathan R Price
*Assistant Examiner* — Melissa A Snyder
(74) *Attorney, Agent, or Firm* — Marshall, Gerstein & Borun LLP

(57) ABSTRACT

A rotatable drive mechanism for a drug delivery device may include a lead screw having a distal end, a proximal end, and external threads, a bearing, and a ball screw driver having a threaded aperture wherein the threaded aperture is configured to rotatably engage with the external threads of the lead screw. The mechanism may further include a biasing device disposed between the bearing and the ball screw driver generating an axial drive force, and an activation device configured to release the biasing device and allowing the biasing device to expand from a compressed position to an extended position through which the axial drive force of the biasing device causes the ball screw driver to axially move toward the distal end of the lead screw and rotate the lead screw such that a threaded engagement between the lead screw and the ball screw driver bears the axial drive force.

33 Claims, 11 Drawing Sheets

(56) References Cited

U.S. PATENT DOCUMENTS

| | | |
|---|---|---|
| 6,979,316 B1 | 12/2005 | Rubin et al. |
| 7,052,484 B2 | 5/2006 | Veasey et al. |
| 7,635,356 B2 | 12/2009 | Stamp |
| 7,654,983 B2 | 2/2010 | De La Sema et al. |
| 7,708,163 B2 | 5/2010 | Argentine |
| 7,785,288 B2 | 8/2010 | Mernøe et al. |
| 7,857,791 B2 | 12/2010 | Jacobs et al. |
| 8,157,769 B2 | 4/2012 | Cabiri |
| 8,262,614 B2 | 9/2012 | Freeman et al. |
| 8,343,109 B2 | 1/2013 | Marshall et al. |
| 8,465,455 B2 | 6/2013 | Cabiri |
| 8,574,215 B2 | 11/2013 | Nason et al. |
| 8,608,708 B2 | 12/2013 | Cowe |
| 8,888,750 B2 | 11/2014 | Veasey et al. |
| 8,939,935 B2 | 1/2015 | O'Connor et al. |
| 9,028,454 B2 | 5/2015 | Veasey et al. |
| 9,168,339 B2 | 10/2015 | Cowe |
| 9,174,005 B2 | 11/2015 | Evans |
| 9,446,195 B2 | 9/2016 | Kramer et al. |
| 9,486,584 B2 | 11/2016 | Julian et al. |
| 9,561,333 B2 | 2/2017 | Cox et al. |
| 9,572,927 B2 | 2/2017 | Bruggemann et al. |
| 2012/0041387 A1 | 2/2012 | Bruggemann et al. |
| 2013/0112521 A1 | 5/2013 | Ekman et al. |
| 2013/0197478 A1 | 8/2013 | Leak et al. |
| 2013/0204204 A1 | 8/2013 | Butler et al. |
| 2013/0245596 A1 | 9/2013 | Cabiri et al. |
| 2015/0119814 A1 | 4/2015 | Fabien et al. |
| 2015/0141923 A1 | 5/2015 | Wurmbauer et al. |
| 2015/0265776 A1 | 9/2015 | Beek et al. |
| 2016/0220764 A1 | 8/2016 | Durvasula et al. |

\* cited by examiner

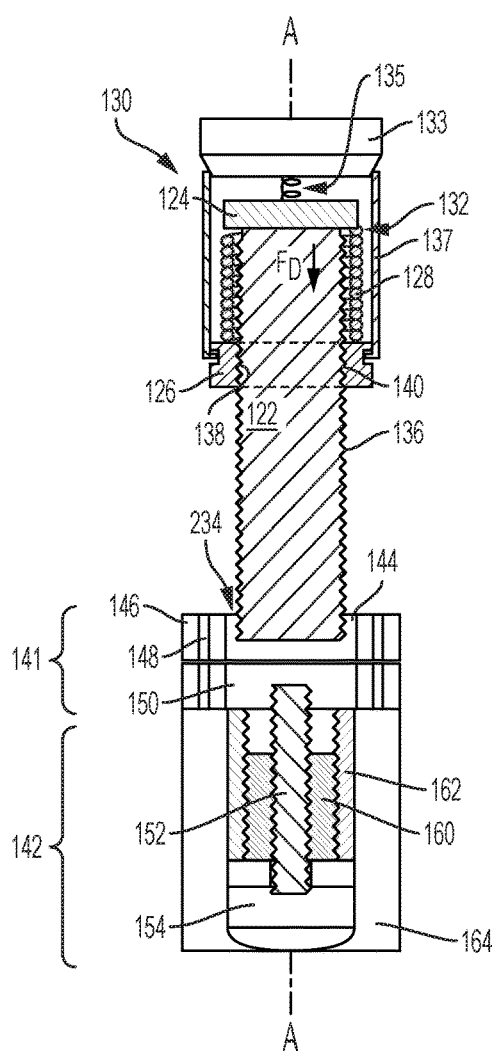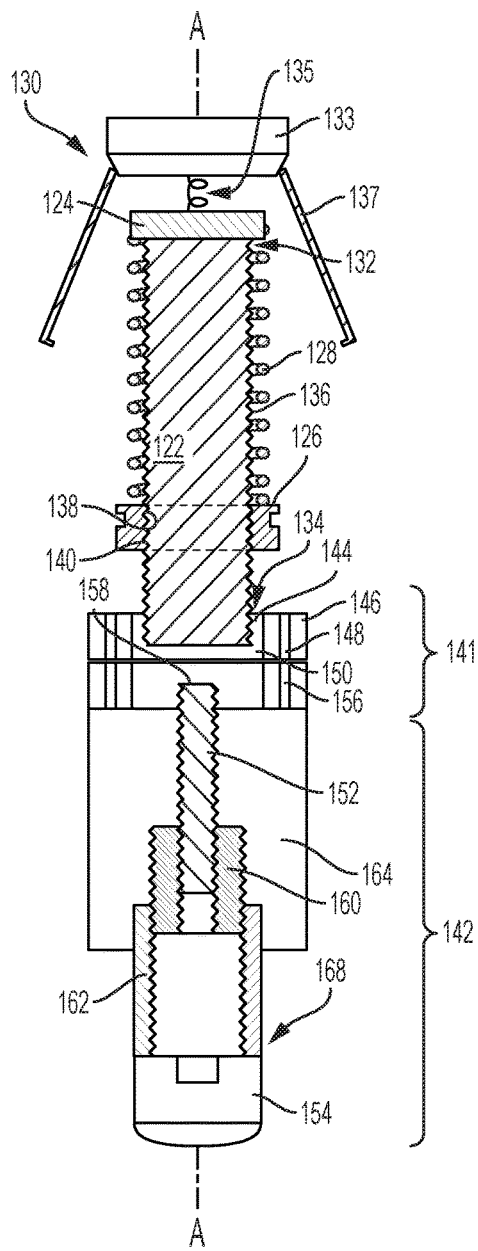
FIG. 4
FIG. 5

X-X

Y-Y

DRUG DELIVERY DEVICE WITH A ROTATABLE DRIVE MECHANISM

CROSS-REFERENCE TO RELATED APPLICATIONS

The priority benefit of U.S. Provisional application Ser. No. 62/365,185, filed Jul. 21, 2016, is hereby claimed and the entire contents are incorporated herein by reference.

FIELD OF TECHNOLOGY

The present disclosure is directed to a drug delivery device and, more particularly, to a drug delivery device with a rotatable drive mechanism having a lead screw.

BACKGROUND

Drug delivery devices, such as autoinjectors and handheld injectors, are commonly prescribed for patients to self-administer medication. Such devices typically include a drive mechanism (e.g., a spring) that operates on a prefilled syringe in response to a triggering event, such as the patient pressing a button on the device. The drive mechanism creates a drive force and, additionally, operates on a plunger to deliver the medication subcutaneously via the needle. These drug delivery devices may be constructed as single-use or reusable devices. Autoinjectors offer several benefits in drug delivery over conventional syringes, such as simplicity of use. Autoinjectors are beneficial for delivering drugs with high viscosities. However, as viscosity increases, the drive force required to inject the drug also increases. A large drive force may cause internal pressure build-up within the device, causing the prefilled syringe to fracture during injection.

FIG. 1 illustrates a known autoinjector 10 that includes a reservoir 12 configured to contain and/or containing a drug 11, a drug delivery member 14 configured to deliver the drug, a plunger rod 16 configured to drive a plunger 18, and a drive mechanism 20 configured to power drug delivery. The reservoir 12 in this example is a glass syringe and includes a thin-walled glass barrel 13.

The drive mechanism 20 includes a compressed coil spring 21 coupled to the plunger rod 16 and is configured to deliver an initial force to move the plunger rod 16 from a preloaded position where the plunger rod 16 is spaced away from the plunger 18, to a second position where the plunger rod 16 makes contact with the plunger 18. Upon actuation of the drive mechanism 20, this conventional autoinjector 10 can experience an impact event (not shown), where the drive force initially causes the plunger rod 16 to impart an impact force on the plunger 18 before causing the plunger 18 to move through the reservoir 12. As the plunger 18 moves through the reservoir 12, a stopper 15 of the plunger 18 is configured to sealingly and slidably engage an inner wall of the glass barrel 13 to push the drug 11 through the reservoir 12 and out through an open end of the drug delivery member 14.

Based on the requirements of the drug 11 and the force generated by the drive mechanism 20 (i.e., a high viscosity drug may require a higher drive force to move the plunger 18 through the reservoir 12), the plunger rod 16 may indirectly or directly impart impact forces onto the barrel 13 of the reservoir 12 when the plunger rod 16 impacts the plunger 18. Large forces could break the barrel 13. If the plunger 18 is placed lower in the reservoir 12, the impact becomes more likely to cause breakage. A load from the impact event generates pressure waves in the drug 11 that propagate through the glass barrel 13. For the combination of materials and geometries typical of glass syringes, a pressure wave will "couple" to the glass barrel 13 of the reservoir 12 as it propagates axially. The coupled wave oscillates through the barrel 13 and may cause the barrel 13 to fracture.

SUMMARY

The present disclosure minimizes the risk of component failure due to impact forces of a spring-loaded drug delivery device. Specifically, the present disclosure includes a drug delivery device with a rotatable drive mechanism that bears the load of the drive force rather than imparting an impact force on a glass-walled reservoir of the drug delivery device. In accordance with one or more aspects described herein, a rotatable drive mechanism of a drug delivery device may provide a safe drive system capable of variable injection rates, deliverable volumes, and drug viscosities without compromising integrity of components of the drug delivery device.

In accordance with a first exemplary aspect, a rotatable drive mechanism for a drug delivery device may include a lead screw having a distal end, a proximal end, and external threads, a bearing operably attached to the proximal end of the lead screw, a ball screw driver having a threaded aperture, wherein the threaded aperture is configured to rotatably engage with the external threads of the lead screw, the ball screw driver and lead screw being coaxially aligned. The drive mechanism may further include a biasing device disposed between the bearing and the ball screw driver generating an axial drive force for biasing the ball screw driver away from the bearing. Further, the drive mechanism may include an activation device configured to release the biasing device and allowing the biasing device to expand from a compressed position to an extended position through which the axial drive force of the biasing device causes the ball screw driver to axially move toward the distal end of the lead screw and rotate the lead screw such that a threaded engagement between the lead screw and the ball screw driver bears the axial drive force.

In accordance with a second exemplary aspect, a drug delivery device may include a reservoir having a distal end and proximal end, a drug delivery member in fluid communication with the distal end of the reservoir, a plunger disposed in and moveable relative to the reservoir, a drive mechanism including a lead screw having a distal end, a proximal end, and external threads, a bearing operably attached to the proximal end of the lead screw, a ball screw driver having a threaded aperture, wherein the threaded aperture is configured to rotatably engage with the external threads of the lead screw, the ball screw driver and lead screw being coaxially aligned, a biasing device disposed between the bearing and the ball screw driver generating an axial drive force for biasing the ball screw driver away from the bearing. The drive mechanism may further include an activation device configured to release the biasing device and allowing the biasing device to expand from a compressed position to an extended position through which the axial drive force of the biasing device causes the ball screw driver to axially move toward the distal end of the lead screw and rotate the lead screw such that a threaded engagement between the lead screw and ball screw driver bears the axial drive force.

In accordance with a third exemplary aspect, a rotatable drive mechanism for a drug delivery device may include a lead screw having a distal end, a proximal end, and external threads, a bearing operably attached to the proximal end of the lead screw, a ball screw driver having a threaded aperture, wherein the threaded aperture is configured to rotatably engage with the external threads of the lead screw, the ball screw driver and lead screw being coaxially aligned, a biasing device disposed between the bearing and the ball screw driver generating an axial drive force for biasing the ball screw driver away from the bearing, and an activation device configured to release the biasing device and allowing the biasing device to expand from a compressed position to an extended position through which the axial drive force of the biasing device causes the ball screw driver to axially move toward the distal end of the lead screw and rotate the lead screw such that a threaded engagement between the lead screw and ball screw driver bears the axial drive force. The rotatable drive mechanism may further include a planetary gear coupler having a sun gear, a plurality of satellites, and a plurality of satellite shafts, wherein the sun gear receives a first rotational velocity from the lead screw and delivers a second rotational velocity to the satellite shafts via the satellites. Further, a telescoping plunger assembly may include an actuator, a plunger rod, and a plunger, the actuator being coupled to the satellite shafts at an input and coupled to the plunger rod at an output, the actuator being configured to receive a rotational velocity from the satellite shafts and deliver a drive force to the plunger rod wherein the plunger rod axially moves the plunger in a distal direction.

In accordance with a fourth aspect, a drug delivery device may include a reservoir containing a drug, a drug delivery member in fluid communication with the reservoir, a plunger disposed in and moveable relative to the reservoir, and a drive mechanism. The drive mechanism may include a lead screw having external threads, and a planetary gear coupler operatively coupled to the external threads of the lead screw. The planetary gear coupler may be configured to drive the lead screw in a axial direction. A biasing device may generate a rotational velocity deliverable to the planetary gear coupler. An activation device may be configured to release the biasing device and allow the biasing device to expand from a compressed position to an extended position through which the rotational velocity of the biasing device causes the lead screw to rotate.

In further accordance with any one or more of the foregoing first, second, third, and fourth aspects, the rotatable drive mechanism for a drug delivery device and a drug delivery device may include any one or more of the following forms.

In one form, the rotatable drive mechanism may include a planetary gear coupler having a carrier arm, a sun gear, a plurality of satellites, and a plurality of connector shafts, wherein the carrier arm may receive a first rotational velocity from the lead screw and delivers a second rotational velocity to the satellites via the connector shafts, wherein the satellites may deliver a third rotational velocity to the sun gear.

In one form, the rotatable drive mechanism may include a plunger rod threadably coupled to the sun gear, wherein the sun gear delivers a fourth rotational velocity to the plunger rod to axially move the plunger rod in a distal direction.

In one form of the drive mechanism, the first rotational velocity may be greater than the second rotational velocity.

In one form of the drive mechanism, the second rotational velocity may be less than the first rotational velocity.

In one form, the drive mechanism may include a clutch mounted to the lead screw to reduce a rotational velocity of the lead screw.

In one form, the clutch may be an electromechanical clutch.

In one form, the drug delivery device may include a plunger rod having a distal end and a proximal end, the distal end of the plunger rod being adjacent to the plunger and the proximal end being adjacent to the ball screw driver, and wherein the ball screw driver is configured to axially move the plunger rod as the ball screw driver axially moves toward the distal end of the lead screw.

In one form, the clutch may further include a dial mechanically coupled to the clutch, wherein the clutch may reduce the rotational velocity of the lead screw at a first rate by rotating the dial to a first position and a second rate when the dial is in a second position.

In one form, the drug delivery device may include a housing containing the planetary gear coupler. The planetary gear coupler may include a planetary ring fixed to the housing, a carrier arm, a sun gear, a plurality of satellites, and a plurality of connector shafts.

In one form of the drug delivery device, the carrier arm may receive a first rotational velocity from the biasing device and delivers a second rotational velocity to the satellites via the connector shafts, and wherein the satellites deliver a third rotational velocity to the sun gear.

In one form of the drug delivery device, the biasing device may be a torsion spring operatively coupled to the planetary gear coupler such that when the activation device releases the torsion spring, the torsion spring causes the planetary gear coupler to rotate the lead screw and drive the lead screw in the axial direction.

In one form of the drug delivery device, the torsion spring may be fixed to the planetary ring and operatively coupled the carrier arm, such that the torsion spring applies a torque to the carrier arm when the torsion spring is released by the activation device.

In one form of the drug delivery device, the lead screw may be threadably coupled to the sun gear, and the sun gear delivers a fourth rotational velocity to the lead screw to axially move the lead screw in the distal direction.

In one form of the drug delivery device, the planetary ring may include a top portion, a bottom portion, and a deformable member disposed between the top and bottom portions, the top portion rotatable relative to the housing and the bottom portion fixed to the housing. The deformable member may be configured to deform and absorb a torsional shock when the torsion spring is released.

In one form of the drug delivery device, the biasing device may be a compression spring.

In one form, the drug delivery device may include a bearing operably attached to a proximal end of the lead screw, and a ball screw driver having a threaded aperture. The threaded aperture may be configured to rotatably engage with the external threads of the lead screw, and the ball screw driver and lead screw may be coaxially aligned. The biasing device may be a compression spring disposed between a bearing and the ball screw driver generating an axial drive force for biasing the ball screw driver away from the bearing.

BRIEF DESCRIPTION OF THE DRAWINGS

It is believed that the disclosure will be more fully understood from the following description taken in conjunction with the accompanying drawings. Some of the drawings may have been simplified by the omission of selected elements for the purpose of more clearly showing other elements. Such omissions of elements in some drawings are not necessarily indicative of the presence or absence of particular elements in any of the example embodiments, except as may be explicitly delineated in the corresponding written description. Also, none of the drawings is necessarily to scale.

FIG. 4 illustrates the rotatable drive mechanism of the first exemplary drug delivery device of FIG. 3 in the preloaded configuration.

FIG. 5 illustrates the rotatable drive mechanism of the first exemplary drug delivery device of FIGS. 3 and 4 in an extended position.

DETAILED DESCRIPTION

Figure 6:
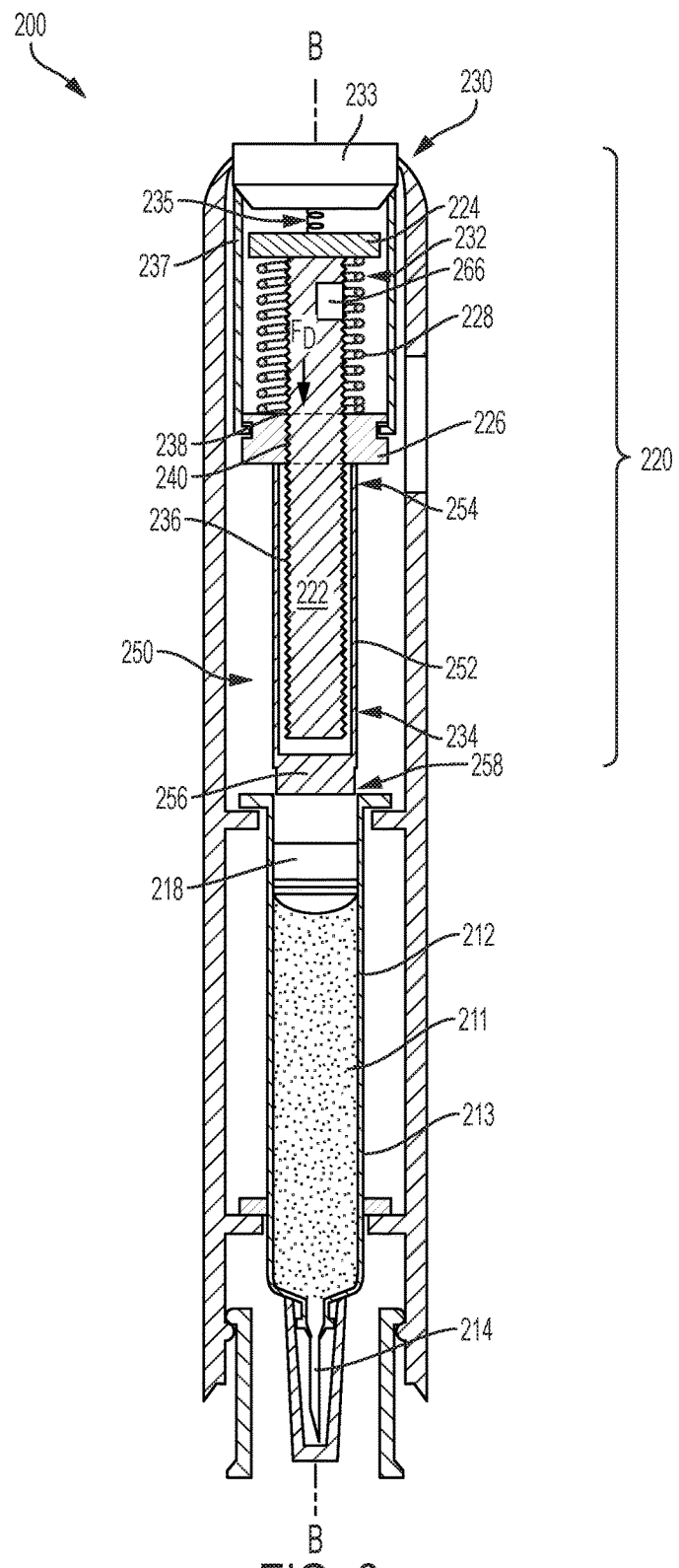
FIG. 6 illustrates a second exemplary drug delivery device having a rotatable drive mechanism with a lead screw in a preloaded configuration.
Figures 7, 8:
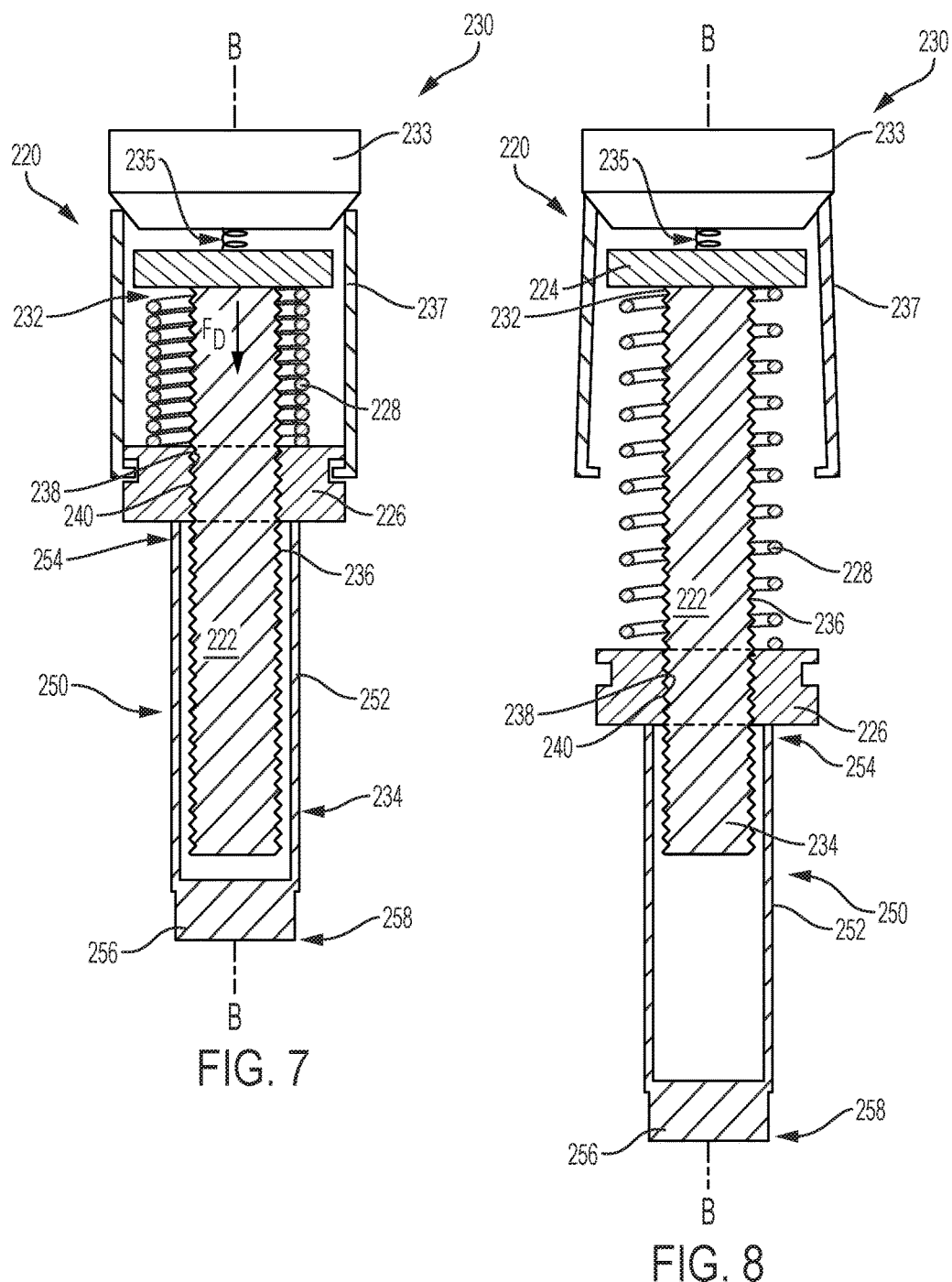
FIG. 7 illustrates the rotatable drive mechanism of the second exemplary drug delivery device of FIG. 6 in the preloaded configuration.
FIG. 8 illustrates the rotatable drive mechanism of the second exemplary drug delivery device of FIGS. 6 and 7 in an extended position.
Figure 9:
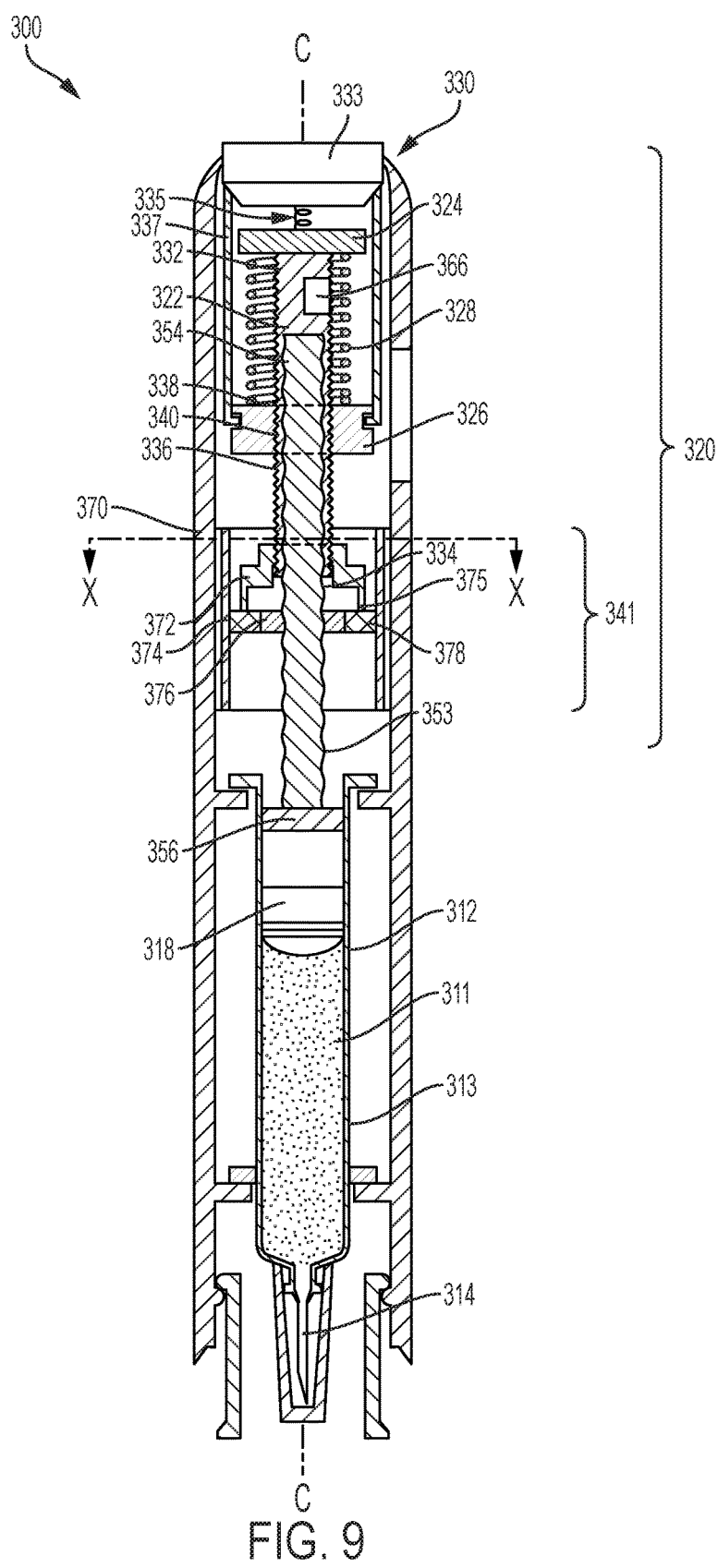
FIG. 9 illustrates a third exemplary drug delivery device having a rotatable drive mechanism with a lead screw and a second exemplary planetary gear coupler power pack in a preloaded configuration.
Figure 10:
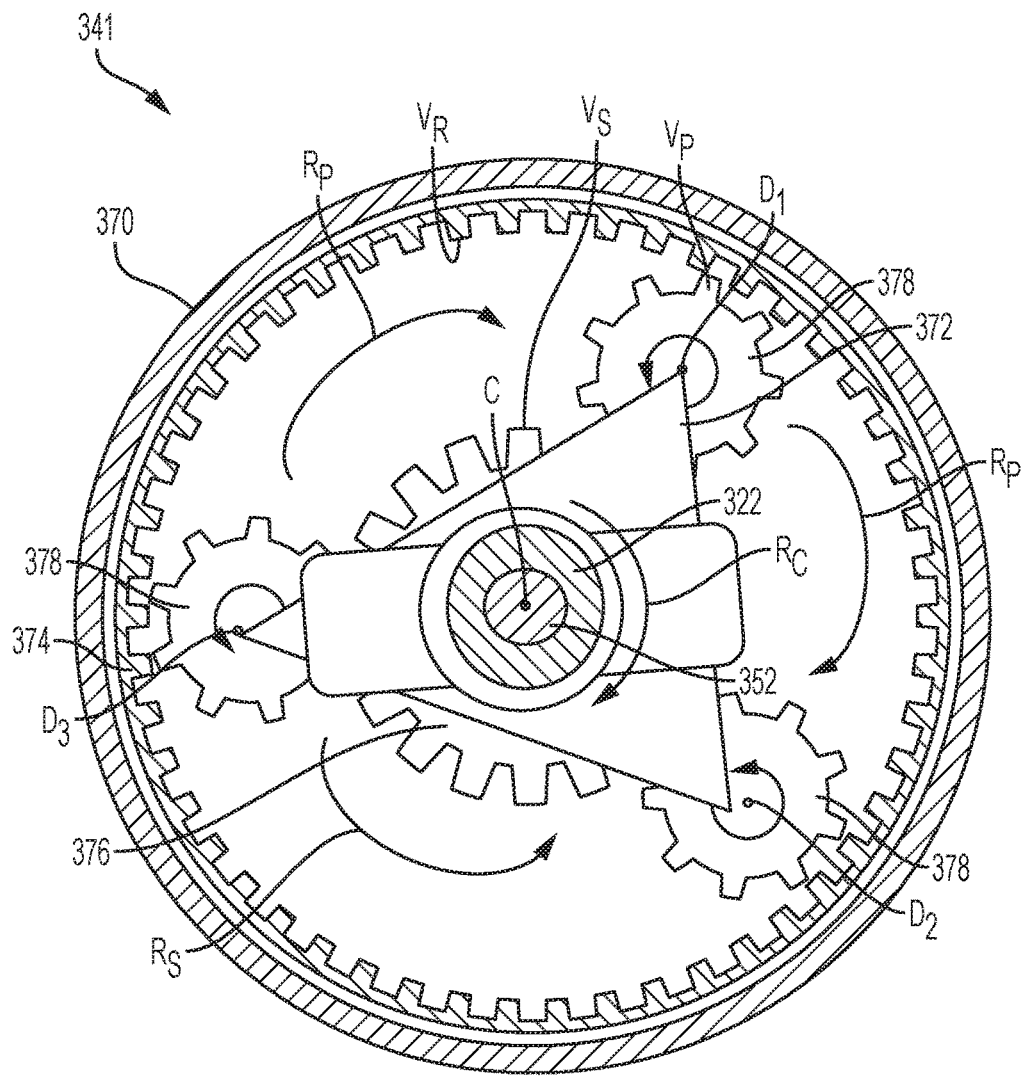
FIG. 10 illustrates a cross-sectional view of the planetary gear coupler power pack of FIG. 9, taken generally along plane X-X.

The rotatable drive mechanisms and drug delivery devices described and illustrated herein allow for variable volume delivery without loading a prefilled syringe. Each of the drug delivery devices includes a rotatable drive mechanism powered by a biasing device, which drives the rotatable drive mechanism to move a lead screw and/or plunger rod for drug delivery. A first exemplary embodiment of a drug delivery device in FIGS. 2-5 has a lead screw and planetary gear coupler power pack, which may be used to control the speed of the plunger rod through the drug delivery device according to the requirements of the drug. In FIGS. 6-8, a second exemplary embodiment of a drug delivery device has a simplified rotatable drive mechanism having a lead screw and plunger assembly. FIGS. 9 and 10 illustrate a third exemplary embodiment of a drug delivery device having a rotatable drive mechanism including a lead screw and a different planetary gear coupler power pack. Finally, FIGS. 11-14 illustrate another embodiment of a drug delivery device with a third exemplary planetary gear coupler power pack used to power drug delivery.

Figure 1:
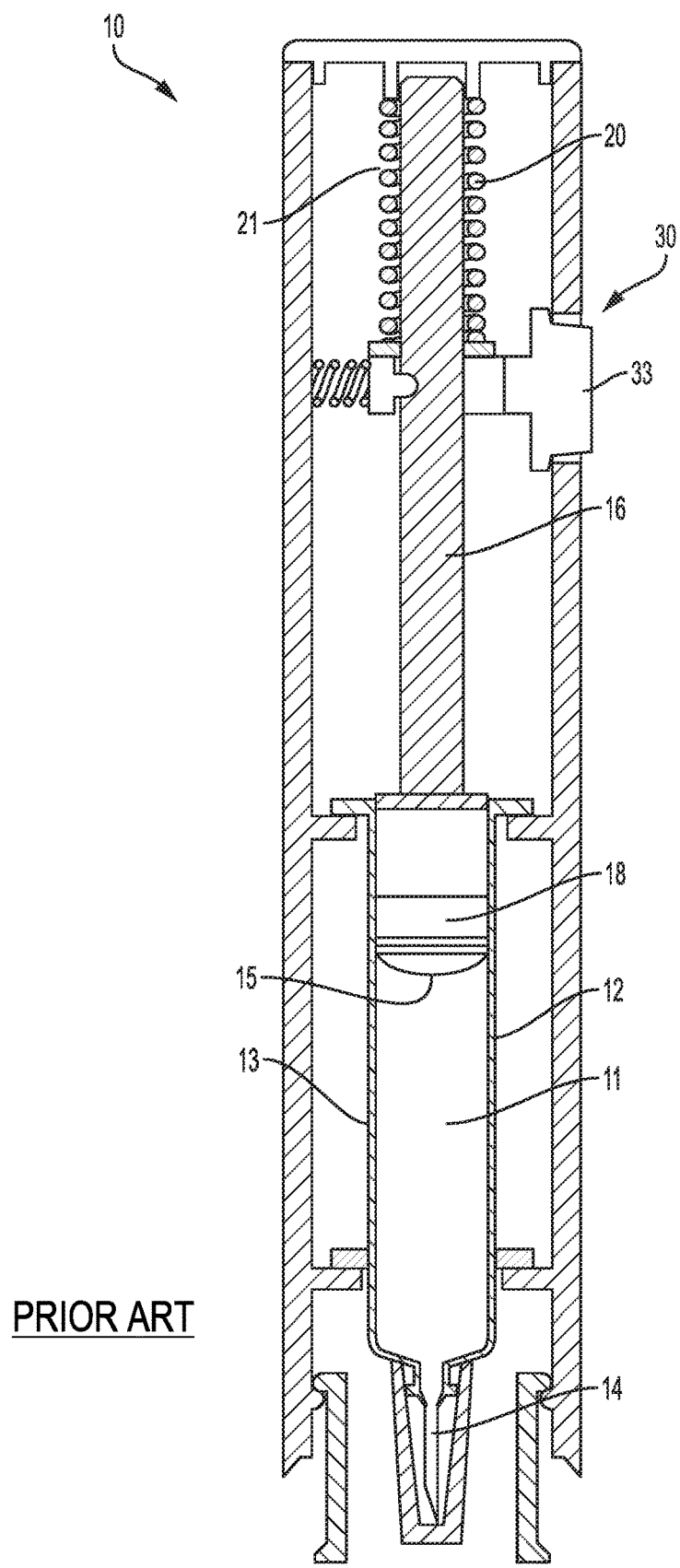
FIG. 1 illustrates a conventional spring-loaded autoinjector susceptible to syringe fracture.
Figure 2:
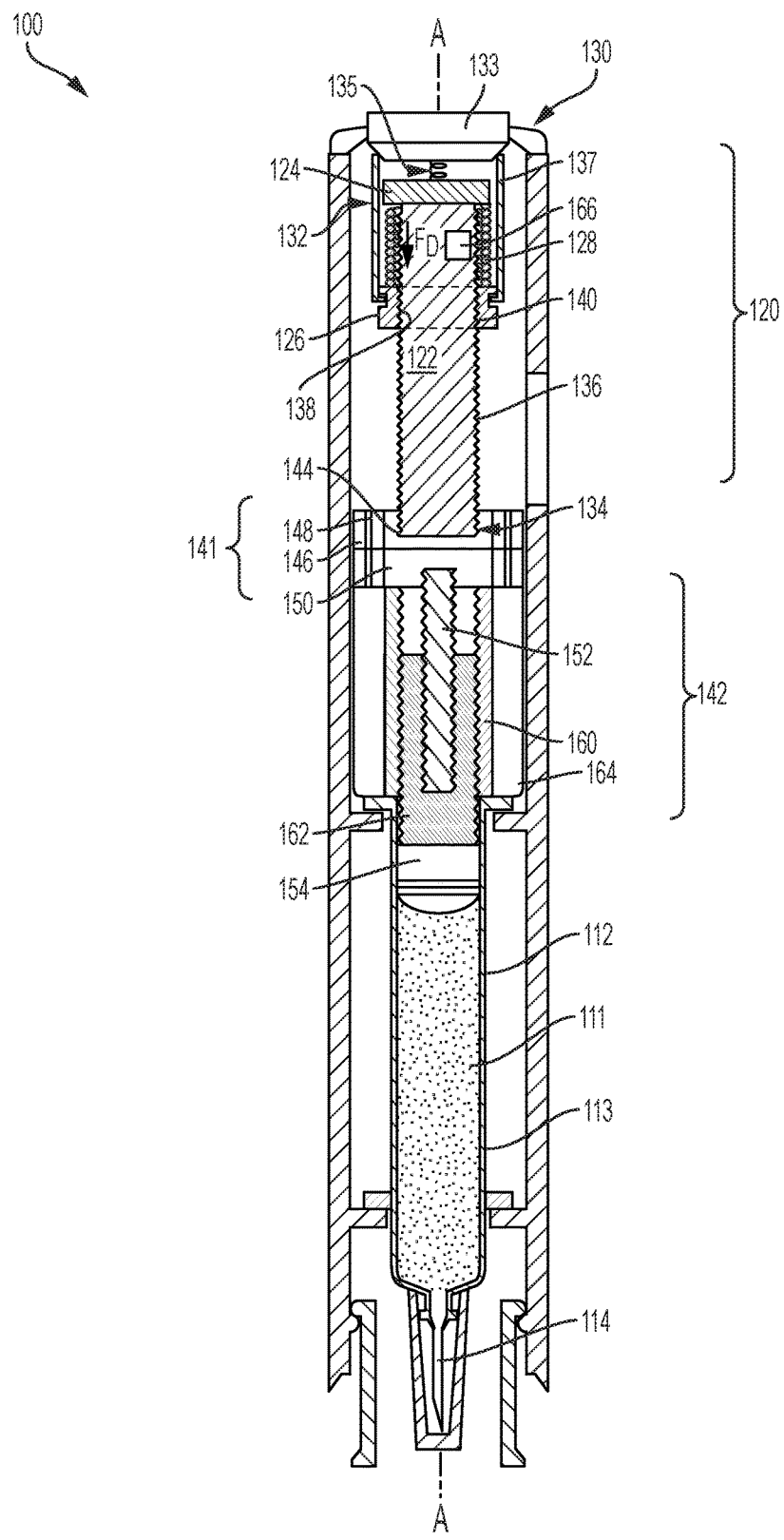
FIG. 2 illustrates a first exemplary drug delivery device having a rotatable drive mechanism with a lead screw and planetary gear coupler power pack in a preloaded configuration.
Figure 3:
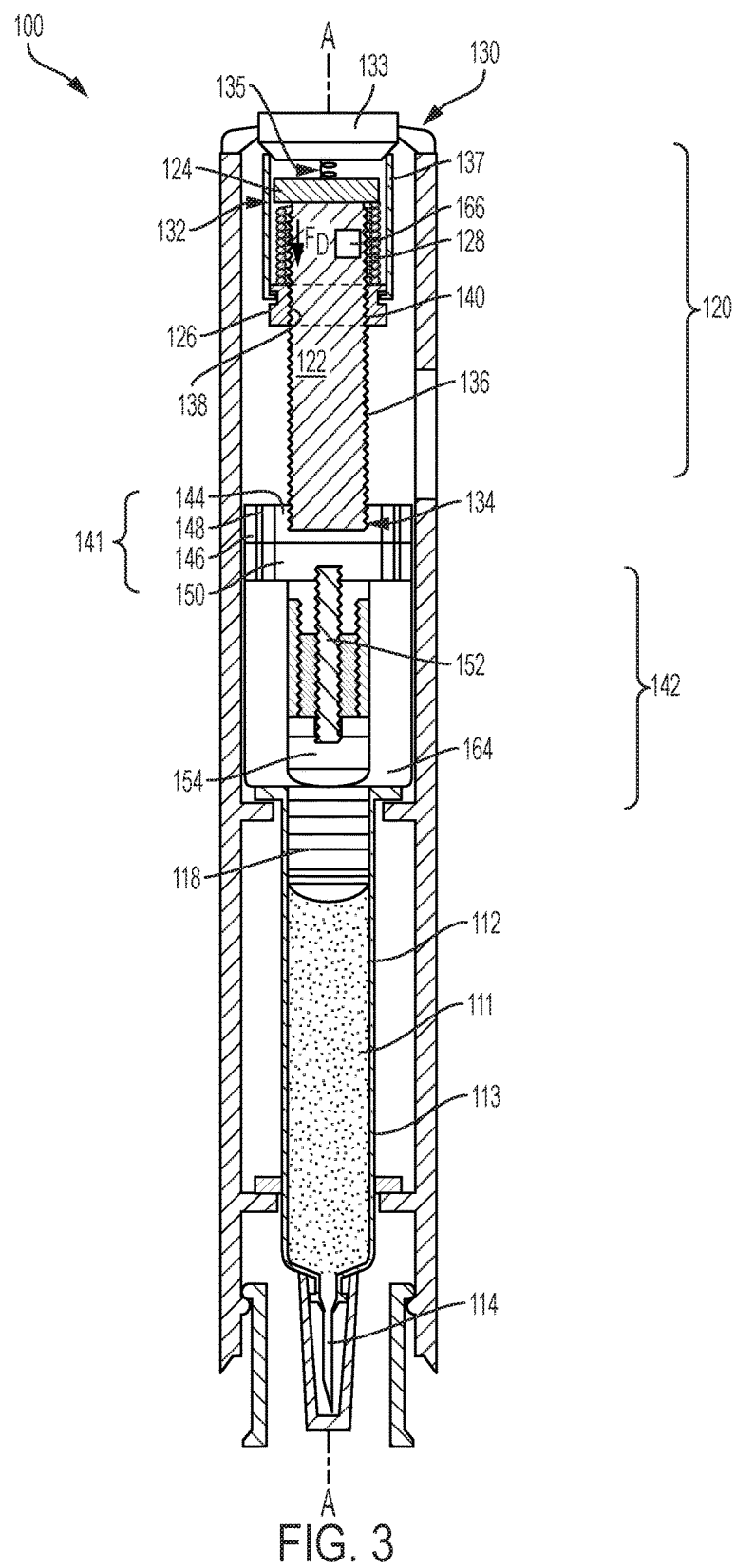
FIG. 3 illustrates a variation of the first exemplary drug delivery device.

Turning first to FIG. 2, the first exemplary drug delivery device 100 includes a rotatable drive mechanism 120 which powers drug delivery. Similar to the drug delivery device 10 of FIG. 1, the drug delivery device 100 includes a drug reservoir 112, which may be a prefilled syringe, and includes a glass cylindrical barrel 113 configured to contain the dispensable fluid 111 until delivery. A drug delivery member 114 is in fluid communication with the reservoir 112 and delivers the dispensable fluid 111 subcutaneously to a patient. A plunger 154 is disposed and movable within the reservoir 112 and is configured to sealingly and slidably engage an inner wall of the barrel 113 to push the drug 111 through the reservoir 112 and out through an open end of the drug delivery member 114. FIG. 3 illustrates a variation on the drug delivery device 100 depicted in FIG. 2 and is identical to the drug delivery device 100 in FIG. 2, but for the fact that it includes an additional stopper 118 that is driven by the plunger 154 through the reservoir 112 by the rotatable drive mechanism 120. The stopper 118 is a separate component from the plunger 154 and is engaged by the plunger 154 during drug delivery.

The rotatable drive mechanism 120 of the drug delivery device 100 shown in FIGS. 2 and 3 is detailed further in FIGS. 4 and 5, and can also be referred to herein as a drive assembly. As shown in FIGS. 2-5, the rotatable drive mechanism 120 includes a lead screw 122, a bearing 124, a ball screw driver 126, a biasing device 128, and an activation device 130. The lead screw 122 is a threaded shaft with a proximal end 132 and a distal end 134, and includes external threads 136 extending between the proximal end 132 and the distal end 134. In other embodiments, the lead screw 122 may be partially threaded. The number of external threads 136 may vary depending on the drive force desired or required for injection and is discussed in more detail below. The ball screw driver 126 includes an aperture 138 having internal threads 140 that engage the external threads 136 of the lead screw 122. The ball screw driver 126 and the lead screw 122 are coaxially aligned along a longitudinal axis A of the drug delivery device 100 when the ball screw driver 126 and the lead screw 122 are threadably engaged.

As illustrated in FIGS. 2-4, the bearing 124 is spaced apart from the ball screw driver 126 by the biasing device 128. The biasing device 128, which is a compressed coil spring, generates an axial drive force $F_D$ for biasing the ball screw driver 126 away from the bearing 124 when released by the activation device 130. The activation device 130 is configured to release the biasing device 128 from the compressed position as shown in FIG. 4, also referred herein as a preloaded configuration, to an extended position as shown in FIG. 5. As the biasing device 128 expands from the compressed position to the extended position, the axial drive force $F_D$ of the biasing device 128 causes the ball screw driver 126 to axially move toward the distal end 134 of the lead screw 122. Simultaneously, a threaded engagement between the external and internal threads 136 and 140 of the lead screw 122 and the ball screw driver 126 causes the lead screw 122 to rotate and bear the axial drive force $F_D$. The bearing 124 is operably attached, either by a ball bearing or other suitable mechanism, to the proximal end 132 of the lead screw 122, allowing the lead screw 122 to freely rotate without moving axially after the biasing device 128 is released. The rotatable drive mechanism 120 of the device in FIGS. 2-5 and, more specifically, the external threads 136 of the lead screw 122, bears the axial drive force $F_D$ instead of the glass barrel 113 of the reservoir 112.

The activation device 130, shown in the preloaded configuration in FIG. 4, includes a button 133, an actuating spring 135, and a plurality of tabs 137. The actuating spring 135 is extended and disposed between the button 133 and the bearing 124. To release the biasing device 128, the button 133 is pressed downward, biasing the actuating spring 135 and causing the button 133 to outwardly displace the tabs 137 away from the ball screw driver 126 and lead screw 122. The biasing device 128 is released by the tabs 127 and expands into the extended position as shown in FIG. 5. The activation device 130 illustrated herein is merely an example, and may be any activation device that can retain the compressed biasing device 128 until it is triggered to release the compressed coil spring 128 for injection.

To vary the rate of injection, the spring rate of the biasing device 128 may be changed, and as mentioned earlier, the external threads 136 of the lead screw 122 and the internal threads 140 of the ball screw driver 126 may also vary. The rotational speed of the lead screw 122 may change by increasing the spacing between threads 136 and/or decreasing or increasing the number of threads 136. In some embodiments, the drug delivery device 100 can also include a power pack that may be changed to vary the injection rate.

For example, the drug delivery device 100 of FIGS. 2-5 includes a planetary gear coupler power pack 141, also referred herein as the planetary gear coupler, that can be used to change the injection rate. The distal end 134 of the lead screw 122 is coupled to the planetary gear coupler power pack 141, which receives an input rotational velocity from the lead screw 122 and delivers a second output velocity. In the illustrated example, the planetary gear coupler power pack 141, also referred herein as a planetary gear coupler, is operably coupled to a telescoping plunger assembly 142 that receives the second output rotational velocity of the power pack 141 and drives the plunger 154 through the reservoir 112. FIG. 4 illustrates an enlarged view of the planetary gear coupler 141 and telescoping assembly 142 when the planetary gear coupler 141 and the telescoping assembly 142 are in a compact configuration. The term "input rotational velocity" is used to describe the rotational velocity of the lead screw 122, and may also be referred to as "input velocity" or "first rotational velocity." The term "output rotational velocity" is used to describe the rotational velocity that the planetary gear coupler 141 delivers after receiving the input rotational velocity, and may also be referred to as a "second velocity" or a "second rotational velocity."

The planetary gear coupler power pack 141 of the drug delivery device 100 described herein is epicyclical and includes a central sun gear 144 and a plurality of orbiting gears 146 that rotate about the sun gear 144. The orbiting gears 146, also referred herein as satellite gears, are smaller in size than the sun gear 144 by a certain degree or gear ratio based on the requirements of the drug delivery device 100. The gear ratio of the satellite gears 146 and the sun gear 144 may vary to either increase or decrease output rotational velocity. The planetary gear coupler 141 of FIGS. 2-5 is a single stage planetary gear coupler 141 in which the input rotational velocity of the lead screw 122 is converted in one stage to either a higher or lower output rotational velocity. Other embodiments may include a multiple-stage planetary gear coupler that may either reduce or magnify the input rotational velocity of the lead screw 122 to varying degrees, which may be controlled by a user by activating or deactivating one or more stages. The planetary gear coupler 141 includes a plurality of satellite shafts 148, each satellite shaft 148 being coaxially aligned with a longitudinal axis of one of the satellite gears 146 and configured to deliver the output rotational velocity. For example, in operation the sun gear 144 receives a first rotational velocity from the lead screw 122 and delivers a second rotational velocity to the satellite shafts 148 via the satellites 146. The satellite shafts 148 deliver the second rotational velocity to the telescoping plunger assembly 142.

FIG. 5 illustrates the biasing device 128 and the telescoping plunger assembly 142 in the extended position. The telescoping plunger assembly 142 in FIGS. 4 and 5 is activated by an actuator 150 and includes a plunger rod 152, the plunger 154, a first telescoping connector 160, and a second telescoping connector 162. The actuator 150 has an input port 156 and an output port 158 where the input port 156 is coupled to the planetary gear coupler 141 via the satellite shafts 148, for example, and the output port 158 is coupled to the plunger rod 152. In operation, the actuator 150 receives an input rotational velocity, e.g. the second rotational velocity, from the satellite shafts 148 and actuates the telescoping plunger assembly 142 in a distal direction. An open sleeve 164 may be attached to the plunger assembly 142 to protect the telescoping plunger assembly from external forces and contamination.

The telescoping plunger assembly 142 may gradually extend from the compressed position shown in FIG. 4, to an extended position shown in FIG. 5 by rotating the plunger rod 152. When the plunger rod 152 rotates, each of the first telescoping connector 160 and the second telescoping connector 162 rotates until each connector occupies the extended position as depicted in FIG. 5. In the example illustrated herein, the actuator 150 rotates the plunger rod 152 relative to the first telescoping connector 160, thereby axially displacing the first telescoping connector 160 in the distal direction until the threads between the rod 152 and connector 160 run out. Further rotation causes the plunger rod 152 and the first telescoping connector 160 to rotate together relative to the second telescoping connector 162, thereby axially displacing the second telescoping connector 162 until the threads between the first telescoping connector 160 and the second telescoping connector 162 run out. That is, the first connector 160 is threadably coupled to the plunger rod 152 so that when the actuator 150 rotates the plunger rod 152, the first connector 160 axially moves in the distal direction until the first connector 160 reaches an end of its axial path. When the first connector 160 reaches the end of its axial path, the first connector 160 begins to rotate together with the plunger rod 152, causing the second connector 162 to axially move in the distal direction. While the illustrated assembly 142 includes two connectors 160 and 162, another embodiment may include two or more connectors where the second connector 162 is connected to a third connector or a series of any number of additional telescoping connectors. The plunger 154, which is attached to a distal end 168 of the second telescoping connector 162, drives through the reservoir 112 to expel the deliverable fluid 111. In FIG. 3, the plunger 154 is adjacent to the stopper 118 and in other embodiments, the plunger 154 may be integrally formed with or otherwise attached to the stopper 118 disposed in the reservoir 112. To bypass the planetary gear coupler altogether, i.e. where the rotational velocity of the lead screw 122 does not need to increase or decrease, the lead screw 122 may be directly coupled to the telescoping plunger assembly 142. The drug delivery device 100 according to the present disclosure is not limited to the telescoping plunger assembly 142 illustrated in FIGS. 2-5, and may include a different assembly that actuates a plunger rod to drive a plunger or stopper through the reservoir 112.

While the illustrated drug delivery device 100 of FIGS. 2-5 includes a telescoping plunger assembly 142 and planetary gear coupler power pack 141, the drive mechanism 120 may be coupled to a different epicyclical power pack and plunger assembly. For example, the rotating lead screw 122 may be operably coupled to a power pack that can receive and convert an input rotational velocity to an output velocity to drive the plunger 154 (or stopper 118 in FIG. 3) of the drug delivery device 100 through the reservoir 112. The rotational speed of the lead screw 122 may be varied by increasing or decreasing the external threads 136 of the screw 122. Additionally, the output rotational velocity may increase or decrease according to changes in gear ratio and number of planetary gear coupler stages. The planetary gear coupler 141 may be configured such that the output rotational velocity is greater than the input velocity, or the planetary gear coupler 141 may be configured such that the input rotational velocity of the lead screw 122 is greater than the output rotational velocity of the planetary gear coupler power pack 141.

Turning back to FIGS. 2 and 3, a clutch 166 may be mounted, or function as a result of the lead screw material, to the lead screw 122 to reduce the rotational velocity of the lead screw 122 after the biasing device 128 is released. The clutch 166 may be a mechanical clutch that provides a dampening or frictional force to the lead screw 122 as the lead screw 122 rotates. For example, the clutch 166 may apply mechanical resistance to the lead screw 122 by frictionally engaging the lead screw 122 and reducing the rotational velocity. The clutch 166 may apply the resistive force to the proximal end 132 or to the external threads 136 of the lead screw 122. For example, in one embodiment, the clutch 166 can include a clutch pad that rests within a recess formed in the proximal end 132 of the lead screw 122 and which is operable through an adjustment mechanism mounted on the drug delivery device 100. The clutch pad can be spring biased against an internal sidewall of the drug delivery device 100 and the lead screw 122, and the adjustment mechanism could include a set screw that adjusts the tension of the spring and therefore the force the clutch pad applies to the lead screw 122. The set screw can in some versions be adjustable with a dial, a knob, or other manual device. In other embodiments, the set screw can be adjustable with an electromechanical switching device. Alternatively, the clutch 166 may be an electromechanical clutch that is electrically operated and applies mechanical resistance to the rotating lead screw 122. For example, the rotating shaft of the lead screw 122 may be aluminum and an applied current creates an electromagnetic flux, producing a regenerative breaking mechanism via eddy currents. Alternatively, the applied current can produce an opposed rotational force to the lead screw 122.

In yet other embodiments, the clutch 166 may be an electromagnetic clutch that generates a magnetic force to reduce the speed of the lead screw 122. For example, the clutch 166 can include a magnet mounted in the proximal end 132 of the lead screw 122 and a coil wrapped around the proximal end 132 of the lead screw 122. Applying a current to the coil creates a magnetic field that can provide a resistance to rotation of the lead screw 122. Increasing the current can increase the resistance, for example. Such an electromagnetic clutch 166 may also be controlled by a dial or other user accessible device for adjusting the clutching force. By rotating the dial to a first position, the clutch may reduce the rotational velocity of the lead screw 122 by a first rate. The dial may be rotated to one of a plurality of positions that correspond to a plurality of varying forces of resistance the clutch 166 may apply to the lead screw 122. In this or in other embodiments, the drug delivery device may include a supercapacitor power source that stores the converted kinetic energy of the biasing device 128 for reuse.

FIG. 6 illustrates a second exemplary drug delivery device 200 having a rotatable drive mechanism 220 which powers drug delivery. For ease of reference, and to the extent possible, the same or similar components of the drug delivery device of FIG. 6 will retain the same reference numbers as outlined above with respect to the drug delivery device 100 of FIG. 2 discussed above, although the reference numbers will be increased by 100. Similar to the drug delivery devices 10 and 100 of FIGS. 1-3, the drug delivery device 200 includes a drug reservoir 212 having a glass barrel 213 that may be prefilled with a dispensable fluid 211. The reservoir 212 is in fluid communication with a drug delivery member 214 through which the dispensable fluid 211 is delivered subcutaneously to a patient. A plunger 218 disposed and movable within the reservoir 212 is configured to sealingly and slidably engage an inner wall of the glass barrel 213 to push the drug 211 through the reservoir 212 and out through an open end of the drug delivery member 214. In the present disclosure, the plunger 218 is driven through the reservoir 212 by the rotatable drive mechanism 220.

The rotatable drive mechanism 220 shown in FIGS. 6-8, also referred herein as a drive assembly, includes a lead screw 222, a bearing 224, a ball screw driver 226, a biasing device 228, and an activation device 230. The lead screw 222 is a threaded shaft with a proximal end 232 and a distal end 234 and includes external threads 236 extending between the proximal and distal ends 232 and 234. In other embodiments, the lead screw 222 may be partially threaded. As described in more detail below, the number of external threads 236 and spacing between the external threads 236 may vary depending on the drive force desired for injection. The ball screw driver 226 includes an aperture 238 having internal threads 240 that engage the external threads 236 of the lead screw 222. The ball screw driver 226 and the lead screw 222 are coaxially aligned along a longitudinal axis B of the drug delivery device 200 when threadably engaged.

As illustrated in FIGS. 6 and 7, the bearing 224 is spaced apart from the ball screw driver 226 by the biasing device 228. The biasing device 228, which is a coil spring, generates an axial drive force $F_D$ for biasing the ball screw driver 226 away from the bearing 224 when released by the activation device 230. The activation device 230 is configured to release the biasing device 228 from the compressed position, as illustrated in FIGS. 6 and 7, to an extended position as shown in FIG. 8. As the biasing device 228 expands from the compressed position, also referred herein as a preloaded position, to the extended position, the axial drive force $F_D$ of the biasing device 228 causes the ball screw driver 226 to axially move toward the distal end 234 of the lead screw 222, while simultaneously causing the lead screw 222 to rotate such that a threaded engagement between the lead screw 222 and the ball screw driver 226 bears the axial drive force $F_D$. The bearing 224 is operably attached, either by a ball bearing or other suitable mechanism, to the proximal end 232 of the lead screw 222, allowing the lead screw 222 to freely rotate without moving axially. The rotatable drive mechanism 220 of the device in FIG. 6, and more specifically the external threads 236 of the lead screw 222, bears the axial drive force $F_D$ instead of the glass barrel 213 of the reservoir 212.

In FIG. 7, the activation device 230 is in the preloaded configuration and includes a button 233, an actuating spring 235, and a plurality of tabs 237. The actuating spring 235 is extended and disposed between the button 233 and the bearing 224. To release the biasing device 228, the button 233 is pressed downward, biasing the actuating spring 235 and outwardly displacing the tabs 237 away from the ball screw driver 226 and lead screw 222. The biasing device 228 is released by the tabs 237 and expands into the extended position as shown in FIG. 8. The activation device 230 illustrated herein is merely an example and may be any device that can retain the compressed biasing device 228 and release the compressed spring 228 to the extended position for injection.

FIGS. 7 and 8 illustrate the drive mechanism 220 in the compressed position (FIG. 7) and in the extended position (FIG. 8). The ball screw driver 226 of the drug delivery device 200 of FIG. 6 may directly apply a drive force to a plunger assembly 250 to drive the plunger 218 through the reservoir 212. The plunger assembly 250 includes a plunger rod 252, which may be a partially hollow cylinder, that surrounds the distal end 232 of the lead screw 222. A proximal end 254 of the plunger rod 252 is adjacent to the ball screw driver 226 and a plunger end 256 is disposed at a distal end 258 of the plunger rod 252. In operation, the activation device 230 releases the biasing device 228, causing the lead screw 222 to rotate and the ball screw driver 226 to axially move in the distal direction. As the ball screw driver 226 moves toward the distal end 234 of the lead screw 222, the ball screw driver 226 drives the plunger rod 252 in the distal direction.

To vary the injection rate, the spring rate of the biasing device 228 may be changed, and as mentioned earlier, the external threads 236 of the lead screw 222 may also vary. The rotational speed of the lead screw 222 may vary by increasing the spacing between threads 236 and/or decreasing or increasing the number of threads 236. For example, the distance travelled by the ball screw driver 226 may be reduced by limiting the extent of coverage of external threads 236 on the lead screw 222. Limiting the threaded coverage of the lead screw 222 limits the distance the ball screw driver 226 can travel in the axial direction, i.e. shortening the axial path of the ball screw driver 226. With fewer external threads 236, the ball screw driver 226 reaches the end of its axial path, i.e. the end of the external threads of the lead screw 222, at a faster rate than if the axial path of the ball screw driver 226 was the entire length of the lead screw 222. The shorter the axial path of the ball screw driver 226, the faster the lead screw 222 rotates, and the greater the force of the ball screw driver 226 imparts onto the plunger rod 252. In contrast, by increasing the number of external threads 236, the ball screw driver 226 would take longer to reach the end of the axial path, thereby decreasing the rate at which the ball screw driver 226 impacts the plunger rod 252.

The plunger assembly 250 may be a single component, as illustrated in FIGS. 6-8, or may be an assembly of separate interconnected components. The plunger rod 252 may be removably attached to the ball screw driver 226 at the proximal end 254 of the plunger rod 252. Alternatively, the proximal end 254 of the plunger rod 252 may be positioned adjacent but not attached to the ball screw driver 226. In the embodiment illustrated in FIGS. 6-8, the plunger end 256 is separate and distinct from the plunger 218 disposed within the reservoir 212. In another embodiment, the plunger end 256 may be integrally formed with the plunger 218.

Turning back to FIG. 6, a clutch 266 may be mounted to the lead screw 222 to reduce the rotational velocity of the lead screw 222 after the biasing device 228 is released. The clutch 266 may be a mechanical clutch that provides a dampening or frictional force to the lead screw 222 as the lead screw 222 rotates. For example, the clutch 266 may apply mechanical resistance to the rotation of the lead screw 222 by frictionally engaging the lead screw 222 and reducing the rotational velocity. The clutch 266 may apply the resistive force to the proximal end 232 of the lead screw 222 or to the external threads 236. Alternatively, the clutch 266 may be a electromechanical clutch that is electrically operated and applies a mechanical resistive force to the rotating lead screw 222. In yet another embodiment, the clutch 266 may be an electromagnetic clutch that directly applies a magnetic force to reduce the speed of the lead screw 222. Although not shown, the clutch 266 may be manually controlled by a dial that is coupled to the clutch 266. By rotating the dial to a first position, the clutch may reduce the rotational velocity of the lead screw 222 by a first rate. The dial may be rotated to one of a plurality of positions that correspond to a plurality of varying forces of resistance the clutch 266 may apply to the lead screw 222.

The drug delivery devices 100 and 200 described herein allow for variations in injection rate, deliverable volume, and drug viscosity. The injection rate may be varied by varying the gearing of the planetary gear coupler power pack 141 of the drug delivery device 100 of FIGS. 2-5 and/or by varying the spring rate of the biasing devices 128 and 228, by varying the configuration of the external threads 136 and 236 of the lead screws 122 and 222, or a combination thereof. The drug delivery devices 100 and 200 do not require a motor nor do they impart a load onto their respective syringes. Rather, the threaded engagement between the lead screw 122 and 222 and the ball screw driver 126 and 226 bear the force of the biasing device 128 and 228, and translate the force to rotational or linear movement. The rotational motion of the lead screw 122 and the linear movement of the ball screw driver 226 provide a low-impact, controlled, and safe drug delivery device.

FIG. 9 illustrates a drug delivery device 300 that may be powered similarly as the drug delivery devices 100 and 200 of FIGS. 2 and 6, but includes a different planetary gear coupler power pack 341, also illustrated in FIG. 10. For ease of reference, and to the extent possible, the same or similar components of the drug delivery device of FIG. 9 will retain the same reference numbers as outlined above with respect to the drug delivery device 100 of FIG. 2 discussed above, although the reference numbers will be increased by 200.

In this embodiment, the planetary gear coupler 341 includes a planetary ring 374, a carrier arm 372, a plurality of connecting shafts 375, satellite gears 378, and a sun gear 376. The planetary ring 374 is fixed to a housing 370 of the device 300, and includes planetary gear teeth $V_R$ which engage with satellite gears teeth $V_P$. The satellite gear teeth $V_P$ also engage with gear teeth $V_S$ of the sun gear 376. When the planetary gear coupler 341 is activated, the carrier arm 372, satellite gears 378, and sun gear 376 rotate either clockwise or counterclockwise about a longitudinal axis C of the drug delivery device 300. The carrier arm 372 is threadably coupled to external threads 336 of a lead screw 322, and rotates in a direction $R_C$ as the lead screw 322 rotates. As the carrier arm 372 rotates in the $R_C$ direction, the connectors shafts 375 connecting the carrier arm 372 and satellite gears 378 cause the satellite gears 378 to rotate around the sun gear 376 in the $R_P$ direction. As the satellite gears 378 rotate in the $R_P$ direction relative to the planetary ring 374, each of the satellite gears 378 spins about its axis D1, D2, and D3, thereby rotating the sun gear 376 in a direction $R_S$. The sun gear 376, which is coupled to external threads 353 of a plunger rod 352, rotates in the $R_S$ direction to drive the plunger rod 352 axially in the distal direction.

Figure 11:
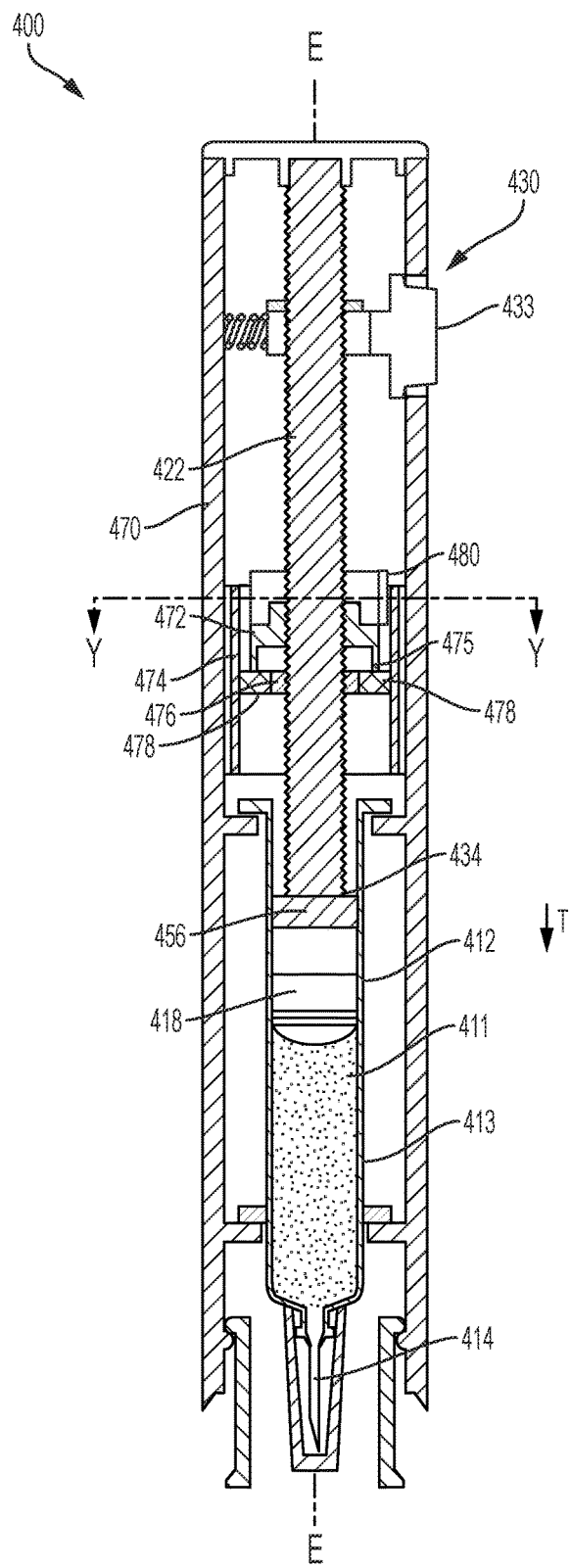
FIG. 11 illustrates a fourth exemplary drug delivery device having a rotatable drive mechanism with a third exemplary planetary gear coupler power pack in a preloaded configuration.
Figure 12:
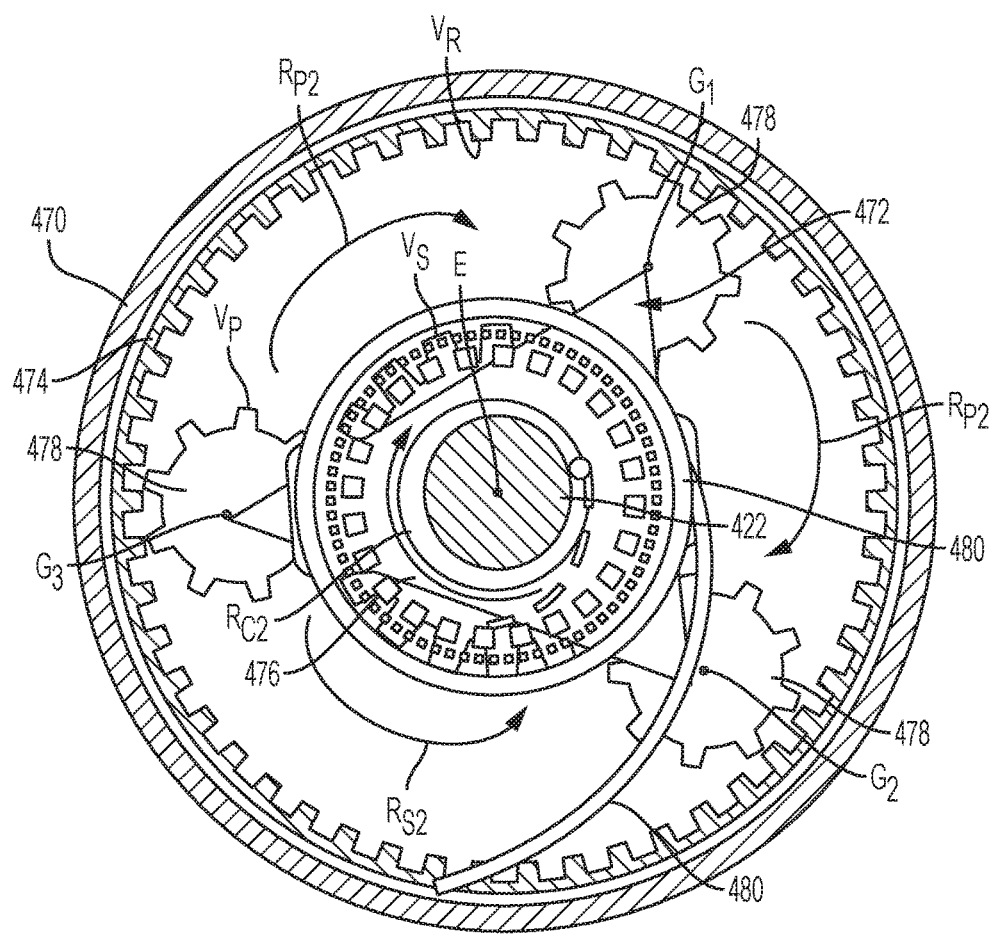
FIG. 12 illustrates a cross-sectional view of the planetary gear coupler power pack of FIG. 11, taken generally along plane Y-Y.

An activation member 330 and a biasing member 328 operate to drive a lead screw driver 326 to spin the lead screw 322 in the same or similar manner as described previously with respect to the drug delivery devices 100 and 200 of FIGS. 2-8. In this embodiment, the lead screw 322 includes a hollow cavity sized to receive a portion of the plunger rod 352. The plunger rod 352 is axially aligned with the lead screw 322 along the longitudinal axis C, and includes external threads 353, a proximal end 354 disposed within the cavity of the lead screw 322, and a distal end 356 disposed within the reservoir 312. The sun gear 376 of the planetary gear coupler 341 is coupled to the external threads 353 of the plunger rod 352, and as the sun gear 376 rotates in the $R_S$ direction, the plunger rod 352 moves in the distal direction and expels the drug 311 contained in the reservoir 312. The planetary gear coupler 141 and 341 of the rotatable drive mechanism 120 and 320 may be used for increasing and/or decreasing the impact of the initial drive force $F_D$ of the biasing device 128 and 328 while providing a sufficient speed to drive the plunger rod through the drug delivery device 100 and 300. In other words, the planetary gear coupler 141 and 341 may be used primarily as a drive transmission, which takes an input rotational velocity of the lead screw 122 and 322 and converts the rotational motion of the lead screw 122 and 322 to linear motion of the plunger rod 152 and 352. Turning now to FIGS. 11 and 12, a different embodiment of a rotatable drive mechanism 420 includes a planetary gear coupler 441 directly coupled to an energy source to power drug delivery of a viscous drug. For ease of reference, and to the extent possible, the same or similar components of the drug delivery device of FIGS. 11 and 12 will retain the same reference numbers as outlined above with respect to the drug delivery device 300 of FIG. 9 discussed above, although the reference numbers will be increased by 100.

The drug delivery device 400 of FIG. 11 is powered by a constant force spring 480, such as a watch spring, torsion spring, or a mechanical polar rotational propulsion source. In the illustrated embodiment, the constant force spring is a torsion spring 480 which applies a constant torque T to the planetary gear coupler 441 of the rotatable drive mechanism 420, which drives a lead screw 422 downward in the axial direction. The torsion spring 480, which is fixed to a stationary planetary ring 474 and attached to a carrier arm 472, pushes against the planetary ring 474 to rotate the carrier arm 472 in the $R_{C2}$ direction about a longitudinal axis E of the drug delivery device 400 when the torsion spring 480 is released. As described previously with respect to the planetary gear coupler 341 of FIGS. 9 and 10, the carrier arm 472 drives a plurality of satellites gears 478 engaged with the planetary ring 474 and a sung gear 476. The carrier arm 472 rotates the satellite gears 478 in an $R_{P2}$ direction, thereby causing the sun gear 476 to rotate in an $R_{S2}$ direction. Each of the satellite gears 478 rotate about its axis $G_1$, $G_2$, and $G_3$ to rotate the sun gear 476 in the $R_{S2}$ direction. As the sun gear 476 spins about the longitudinal axis E in the $R_{S2}$ direction, the lead screw 422, which may be attached to or integral with a plunger rod, moves in the distal direction through the reservoir 412.

In the illustrated embodiment, the torsion spring 480 is indirectly coupled to an activation member 430, which holds the lead screw 422 stationary until the drug delivery device 400 is activated. Although the activation member 430 in this embodiment is similar to the activation member 30 of FIG. 1, the activation member 430 may be any mechanism known in the art capable of releasing the torsion spring 480 on demand. Here, when a button 433 is pushed, the lead screw 422 is free to move, permitting the torsion spring 480 to expand from an initial compressed configuration to an expanded configuration. However, in another embodiment, the activation member 430 may be directly coupled to the torsion spring 480 so that the torsion spring 480 is held in the compressed configuration until the activation member 430 is activated.

Figure 13:
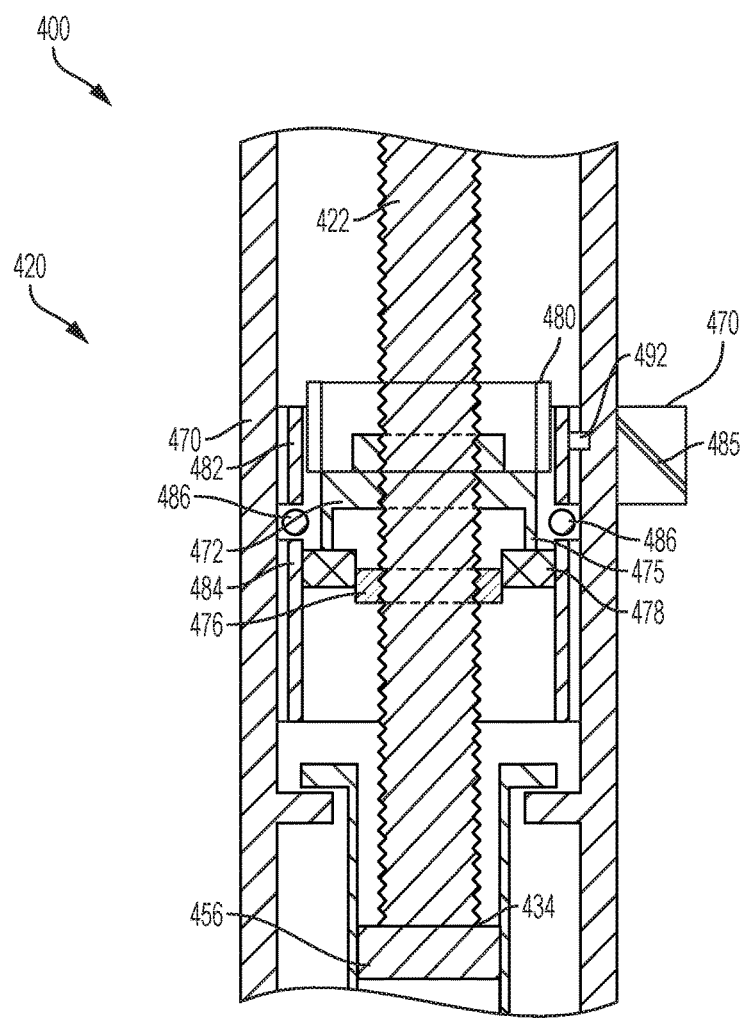
FIG. 13 illustrates a partial view of a variation of the third exemplary planetary gear coupler power pack of FIG. 11 having a shock absorber.
Figure 14:
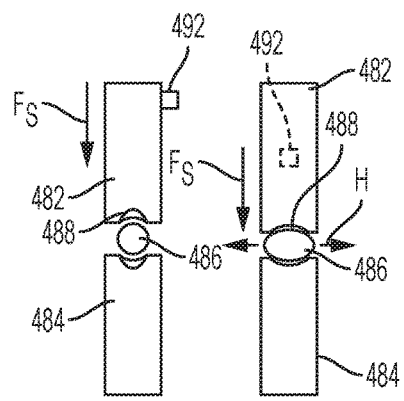
FIG. 14 illustrates a schematic of the shock absorber in the variation of the third exemplary planetary gear coupler power pack of FIG. 13.

To buffer the force of torque T provided by the torsion spring 480, the planetary gear coupler 441 may incorporate a buffer element 486 as shown in a variation of the drug delivery device 400 in FIGS. 13 and 14. The planetary gear coupler 441 differs slightly from the planetary gear coupler 441 of FIGS. 11 and 12, and is arranged differently in an initial configuration and includes a split planetary ring 474. The carrier arm 472 and satellite gears 478 are slightly elevated relative to the sun gear 476, and the split planetary ring 474 includes a first portion 482 and a bottom portion 484 separated by a deformable buffer element 486. The deformable buffer element 486 and the misaligned configuration of the planetary gear coupler 441 allow for the planetary gear coupler 441 to absorb any initial torsional shock of the torsion spring 480, and provide a clutching effect to the rotatable drive mechanism 420.

The bottom portion 484 of the planetary ring 474 is fixed to a housing 470 of the drug delivery device 400, and the top portion 482 of the ring 474 is rotatable relative to the housing 470. The top portion 482 includes a tab 492 extending from the top portion 482 of the planetary ring 474 and disposed within a slotted groove 485 formed in the housing 470 and shaped to guide the tab 492. So configured, as the torsion gear 480 is released, the tab 492 of the top portion 482 of the planetary ring 474 the follows the slotted guide 485 of the housing 470, causing the top portion 482 to rotate and travel downwardly to squeeze the buffer element 486 between the top and bottom portions 482 and 484 of the planetary ring 474. As shown in the schematic of FIG. 14, the top portion 482 of the planetary ring 474 moves downward, compressing the buffer element 486. Once the buffer element 486 reaches a particular point of compression, the top portion 482 no longer rotates and the satellite gears 478 are aligned with the sun gear 476. The buffer element 486 is disposed between a flexible washer 488, which also deforms as the top and bottom portions 482 and 484 squeeze the buffer element 486 to absorb the torsional shock. The buffer element 486 may be an O-ring, bushing, washer, or other pliable material or seal, such as Teflon.

The planetary gear couplers 141, 341, and 441 described herein are configured to reduce overall weight of the mechanical power source of the drug delivery device 100, 300, 400, increase torque output, and/or increase output velocity. The gear teeth ratios of the satellite gears 146, 378, and 478, sun gears 144, 376, and 476, and planetary ring 374 and 474 are determined to achieve any or all of these factors. In a preferred embodiment of the planetary gear couplers 341 and 441, the planetary ring 374 and 474 are held stationary (or at least partially stationary, as illustrated in FIGS. 13 and 14), and the gear teeth ratios of each gear may be the following: gear teeth $V_S$ of the sun gear 376 and 476 is 20; gear teeth $V_R$ of the planetary ring 374 and 474 is 48; gear teeth $V_P$ of the satellite gears 378 and 478 is 16. This ratio may be found to increase torque output by 25% and decrease velocity by 20% without increasing the overall weight of the drug delivery device 300 and 400. While the planetary ring 374 and 474 is stationary in each of the planetary gear couplers 341 and 441, the sun gear 376 and 476, may instead be held stationary. As such, the gear ratios of each gear would be altered accordingly to achieve the desired output velocity, torque, and/or overall weight.

The above description describes various systems for use with a drug delivery device. It should be clear that the drug delivery device can further comprise use of a medicament listed below with the caveat that the following list should neither be considered to be all inclusive nor limiting. The medicament will be contained in a reservoir. In some instances, the reservoir is a primary container that is either filled or pre-filled for treatment with the medicament. The primary container can be a cartridge or a pre-filled syringe.

For example, the drug delivery device or more specifically the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgastrim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of SEQ ID NOS:305-351, including TN8-19-1 through TN8-19-40, TN8-19 con1 and TN8-19 con2; peptibodies of the mL2 family of SEQ ID NOS:357-383; the mL15 family of SEQ ID NOS:384-409; the mL17 family of SEQ ID NOS:410-438; the mL20 family of SEQ ID NOS:439-446; the mL21 family of SEQ ID NOS:447-452; the mL24 family of SEQ ID NOS:453-454; and those of SEQ ID NOS:615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2xL1(N); 2xL1(N) WT; Con4 (N), Con4 (N) 1K WT, 2xCon4 (N) 1K; L1C; L1C 1K; 2xL1C; Con4C; Con4C 1K; 2xCon4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; Ab1A1; Ab1F; Ab1K, Ab1P; and Ab1P, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present invention are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (?4), deposited at the ATCC under number PTA-5214, and a light chain encoded by a polynucleotide in plasmid 15H12/19D12 LCF (?), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of SEQ ID NO:17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-?4ß7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNF? monoclonal antibody); Reopro® (abciximab, anti-GP IIb/IIia receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-?4integrin mAb); Valortim® (MDX-1303, anti-B. anthracis protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2R? mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNF? mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-?5?1 integrin mAb); MDX-010 (ipilimumab, anti-CTLA-4 mAb and VEGFR-1 (IMC-18F1); anti-BR3 mAb; anti-C. difficile Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxinl mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFN? mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-W10 Ulcerative Colitis mAb (MDX-1100);

anti-LLY antibody; BMS-66513; anti-Mannose Receptor/ hCG? mAb (MDX-1307); anti-mesothelin dsFv-PE38 conjugate (CAT-5001); anti-PD1mAb (MDX-1106 (ONO-4538)); anti-PDGFR? antibody (IMC-3G3); anti-TGFß mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab), as well as molecules, variants, analogs or derivatives thereof as disclosed in the following patents or patent applications, each of which is herein incorporated by reference in its entirety for all purposes: U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223, 593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, bispecific T cell engager (BiTE®) antibodies, e.g. BLINCYTO® (blinatumomab), can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

At least some of the techniques of this disclosure similarly can be applied to other drug delivery devices. For example, drug delivery devices generally suitable for simulation using the techniques of this disclosure can include other hand-held injectors or on-body injectors. More generally, the techniques of this disclosure can be applied to devices in which a component that advances a liquid drug (or another liquid) uses coil compression, torsion, or another type of mechanical energy storage. Moreover, these techniques can be applied to non-mechanical systems such as propellant-driven systems.

Although the autoinjectors and elements thereof, have been described in terms of exemplary embodiments, they are not limited thereto. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent that would still fall within the scope of the claims defining the invention.

It should be understood that the legal scope of the invention is defined by the words of the claims set forth at the end of this patent application. The appended claims should be construed broadly to include other variants and embodiments of same, which may be made by those skilled in the art without departing from the scope and range of equivalents of autoinjectors and their elements.

What is claimed:

1. A rotatable drive mechanism for a drug delivery device, the drive mechanism comprising:
   a lead screw having a distal end, a proximal end, and external threads;
   a bearing operably attached to the proximal end of the lead screw;
   a ball screw driver having a threaded aperture, wherein the threaded aperture is configured to rotatably engage with the external threads of the lead screw, the ball screw driver and lead screw being coaxially aligned;
   a biasing device disposed between the bearing and the ball screw driver generating an axial drive force for biasing the ball screw driver away from the bearing; and
   an activation device configured to release the biasing device and allow the biasing device to expand from a compressed position to an extended position through which the axial drive force of the biasing device causes the ball screw driver to axially move toward the distal end of the lead screw and rotate the lead screw such that a threaded engagement between the lead screw and the ball screw driver bears the axial drive force.

2. The rotatable drive mechanism of claim 1, further comprising a planetary gear coupler having a sun gear, a plurality of satellites, and a plurality of satellite shafts, wherein the sun gear receives a first rotational velocity from the lead screw and delivers a second rotational velocity to the satellite shafts via the satellites.

3. The rotatable drive mechanism of claim 2, further comprising a telescoping plunger assembly comprising an actuator, a plunger rod, and a plunger, the actuator being coupled to the satellite shafts at an input and coupled to the plunger rod at an output, the actuator being configured to receive a rotational velocity from the satellite shafts and axially moves the plunger rod and the plunger in a distal direction.

4. The rotatable drive mechanism of claim 1, further comprising a planetary gear coupler having a carrier arm, a sun gear, a plurality of satellites, and a plurality of connector shafts, wherein the carrier arm receives a first rotational velocity from the lead screw and delivers a second rotational velocity to the satellites via the connector shafts, wherein the satellites deliver a third rotational velocity to the sun gear.

5. The rotatable drive mechanism of claim 4, further comprising a plunger rod threadably coupled to the sun gear, wherein the sun gear delivers a fourth rotational velocity to the plunger rod to axially move the plunger rod in a distal direction.

6. The rotatable drive mechanism of claim 2, wherein the first rotational velocity is greater than the second rotational velocity.

7. The rotatable drive mechanism of claim 2, wherein the second rotational velocity is less than the first rotational velocity.

8. The rotatable drive mechanism of claim 1, further comprising a clutch mounted to the lead screw to reduce a rotational velocity of the lead screw.

9. The rotatable drive mechanism of claim 8, wherein the clutch is an electromechanical clutch.

10. A drug delivery device comprising:
a reservoir having a distal end and proximal end;
a drug delivery member in fluid communication with the distal end of the reservoir;
a plunger disposed in and moveable relative to the reservoir;
a drive mechanism including:
a lead screw having a distal end, a proximal end, and external threads,
a bearing operably attached to the proximal end of the lead screw,
a ball screw driver having a threaded aperture, wherein the threaded aperture is configured to rotatably engage with the external threads of the lead screw, the ball screw driver and lead screw being coaxially aligned, and
a biasing device disposed between the bearing and the ball screw driver generating an axial drive force for biasing the ball screw driver away from the bearing; and
an activation device configured to release the biasing device and allowing the biasing device to expand from a compressed position to an extended position through which the axial drive force of the biasing device causes the ball screw driver to axially move toward the distal end of the lead screw and rotate the lead screw such that a threaded engagement between the lead screw and ball screw driver bears the axial drive force.

11. The drug delivery device of claim 10, further comprising:
a planetary gear coupler operably coupled to the distal end of the lead screw and a telescoping plunger assembly, the planetary gear coupler configured to receive a first rotational velocity of the lead screw and deliver a second rotational velocity to actuator, the actuator configured to convert the second rotational velocity to axial movement of the plunger through the reservoir; and
wherein the first rotational velocity is different from the second rotational velocity.

12. The drug delivery device of claim 11, wherein the planetary gear coupler comprises a sun gear, a plurality of satellites, and a plurality of satellite shafts, wherein the sun gear receives the first rotational velocity from the lead screw and delivers the second rotational velocity to the satellite shafts via the satellites.

13. The drug delivery device of claim 12, further comprising a telescoping plunger assembly comprising an actuator and a plunger rod operably coupled to the plunger, the actuator being coupled to the satellite shafts at an input and coupled to the plunger rod at an output, the actuator being configured to receive a rotational velocity from the satellite shafts and deliver a drive force to the plunger rod wherein the plunger rod axially moves the plunger in a distal direction.

14. The drug delivery device of claim 10, further comprising a plunger rod having a distal end and a proximal end, the distal end of the plunger rod being adjacent to the plunger and the proximal end being adjacent to the ball screw driver, and wherein the ball screw driver is configured to axially move the plunger rod as the ball screw driver axially moves toward the distal end of the lead screw.

15. The drug delivery device of claim 10, further comprising a clutch mounted to the lead screw to reduce a rotational velocity of the lead screw.

16. The drug delivery device of claim 15, wherein the clutch is an electromechanical clutch.

17. The drug delivery device of claim 10, further comprising a planetary gear coupler having a carrier arm, a sun gear, a plurality of satellites, and a plurality of connector shafts, wherein the carrier arm receives a first rotational velocity from the lead screw and delivers a second rotational velocity to the satellites via the connector shafts, wherein the satellites deliver a third rotational velocity to the sun gear.

18. The drug delivery device of claim 17, comprising a plunger rod disposed within a hollow cavity of the lead screw and threadably coupled to the sun gear, wherein the sun gear delivers a fourth rotational velocity to the plunger rod to axially move the plunger rod in a distal direction.

19. A rotatable drive mechanism for a drug delivery device, the drive mechanism comprising:
a lead screw having a distal end, a proximal end, and external threads;
a bearing operably attached to the proximal end of the lead screw;
a ball screw driver having a threaded aperture, wherein the threaded aperture is configured to rotatably engage with the external threads of the lead screw, the ball screw driver and lead screw being coaxially aligned;
a biasing device disposed between the bearing and the ball screw driver generating an axial drive force for biasing the ball screw driver away from the bearing;
an activation device configured to release the biasing device and allowing the biasing device to expand from a compressed position to an extended position through which the axial drive force of the biasing device causes the ball screw driver to axially move toward the distal end of the lead screw and rotate the lead screw such that a threaded engagement between the lead screw and ball screw driver bears the axial drive force;

a planetary gear coupler having a sun gear, a plurality of satellites, and a plurality of satellite shafts, wherein the sun gear receives a first rotational velocity from the lead screw and delivers a second rotational velocity to the satellite shafts via the satellites; and a telescoping plunger assembly comprising an actuator, a plunger rod, and a plunger, the actuator being coupled to the satellite shafts at an input and coupled to the plunger rod at an output, the actuator being configured to receive a rotational velocity from the satellite shafts and deliver a drive force to the plunger rod wherein the plunger rod axially moves the plunger in a distal direction.

20. The rotatable drive mechanism of claim 19, wherein the first rotational velocity is greater than the second rotational velocity.

21. The rotatable drive mechanism of claim 19, wherein the second rotational velocity is less than the first rotational velocity.

22. The rotatable drive mechanism of claim 19, further comprising a clutch mounted to the lead screw to reduce a rotational velocity of the lead screw.

23. The rotatable drive mechanism of claim 22, wherein the clutch is an electromechanical clutch.

24. The rotatable drive mechanism of claim 22, further comprising a dial mechanically coupled to the clutch, wherein the clutch may reduce the rotational velocity of the lead screw at a first rate by rotating the dial to a first position and a second rate when the dial is in a second position.

25. A drug delivery device comprising:
a reservoir having containing a drug;
a drug delivery member in fluid communication with the reservoir;
a plunger disposed in and moveable relative to the reservoir;
a drive mechanism including:
  a lead screw having external threads;
  a planetary gear coupler operatively coupled to the external threads of the lead screw, the planetary gear coupler configured to drive the lead screw in a axial direction;
  a biasing device generating a rotational velocity deliverable to the planetary gear coupler; and
  an activation device to release the biasing device and allow the biasing device to expand from a compressed position to an extended position through which the rotational velocity of the biasing device causes the lead screw to rotate.

26. The drug delivery device of claim 25, further comprising a housing containing the planetary gear coupler, wherein the planetary gear coupler includes a planetary ring fixed to the housing, a carrier arm, a sun gear, a plurality of satellites, and a plurality of connector shafts.

27. The drug delivery device of claim 26, wherein the carrier arm receives a first rotational velocity from the biasing device and delivers a second rotational velocity to the satellites via the connector shafts, and wherein the satellites deliver a third rotational velocity to the sun gear.

28. The drug delivery device of claim 27, wherein the biasing device is a torsion spring operatively coupled to the planetary gear coupler such that when the activation device releases the torsion spring, the torsion spring causes the planetary gear coupler to rotate the lead screw and drive the lead screw in the axial direction.

29. The drug delivery device of claim 28, wherein the torsion spring is fixed to the planetary ring and operatively coupled the carrier arm, such that the torsion spring applies a torque to the carrier arm when the torsion spring is released by the activation device.

30. The drug delivery device of claim 29, wherein the lead screw is threadably coupled to the sun gear, and the sun gear delivers a fourth rotational velocity to the lead screw to axially move the lead screw in the axial direction.

31. The drug delivery device of claim 30, wherein the planetary ring includes a top portion, a bottom portion, and a deformable member disposed between the top and bottom portions, the top portion rotatable relative to the housing and the bottom portion fixed to the housing; and
  wherein the deformable member is configured to deform and absorb a torsional shock when the torsion spring is released.

32. The drug delivery device of claim 25, wherein the biasing device is a compression spring.

33. The drug delivery device of claim 32, comprising a bearing operably attached to a proximal end of the lead screw;
  a ball screw driver having a threaded aperture, wherein the threaded aperture is configured to rotatably engage with the external threads of the lead screw, the ball screw driver and lead screw being coaxially aligned; and
  wherein the biasing device is a compression spring disposed between a bearing and the ball screw driver generating an axial drive force for biasing the ball screw driver away from the bearing.

* * * * *